(12) United States Patent
Taylor

(10) Patent No.: US 7,335,158 B2
(45) Date of Patent: Feb. 26, 2008

(54) SURGICAL DEVICES FOR IMPOSING A NEGATIVE PRESSURE TO STABILIZE THE CARDIAC TISSUE DURING SURGERY

(75) Inventor: Charles S. Taylor, San Francisco, CA (US)

(73) Assignee: Cardiothoracic Systems, Inc., San Jose, CA (US)

( * ) Notice: Subject to any disclaimer, the term of this patent is extended or adjusted under 35 U.S.C. 154(b) by 0 days.

(21) Appl. No.: 10/216,616

(22) Filed: Aug. 8, 2002

(65) Prior Publication Data

US 2003/0036677 A1    Feb. 20, 2003

Related U.S. Application Data

(60) Continuation of application No. 09/440,106, filed on Nov. 15, 1999, now Pat. No. 6,852,075, which is a division of application No. 08/870,687, filed on Jun. 6, 1997, now Pat. No. 6,032,672, which is a division of application No. 08/603,328, filed on Feb. 20, 1996, now Pat. No. 5,727,569.

(51) Int. Cl.
*A61F 2/00* (2006.01)
*A13F 13/00* (2006.01)
*A61B 17/00* (2006.01)
*A61B 19/00* (2006.01)

(52) U.S. Cl. .............. 600/37; 606/1; 128/897
(58) Field of Classification Search .......... 600/37; 294/64.1–64.3
See application file for complete search history.

(56) References Cited

U.S. PATENT DOCUMENTS 452,131 A    5/1891    Haughawout (Continued)

FOREIGN PATENT DOCUMENTS

DE    31 38 589 A1    4/1983

(Continued)

OTHER PUBLICATIONS

Akins, et al. "Preservation of interventricular septal function in patients having coronary artery bypass grafts without cardiopulmonary bypass," *American Heart Journal*, (1984) vol. 107(2): 304-309.

(Continued)

*Primary Examiner*—Charles A. Marmor, II
(74) *Attorney, Agent, or Firm*—Law Office of Alan W. Cannon

(57) ABSTRACT

The invention is devices and techniques which use a negative (suction) pressure or vacuum, applied through a surgical instrument, to fix the position of a portion of the surface of a beating heart so that a surgical procedure can be more easily performed. The devices apply a negative pressure at several points on the outer surface of the heart such that a portion of the heart is fixed in place by the suction imposed through the surgical instrument. Because the instrument fixes the position of the tissue, and because the instruments remain at a constant distance from the particular portion of the heart where the surgery is being performed, the device may also serve as a support or platform so that other surgical instruments or devices can be advantageously used at the site. In certain preferred embodiments, the devices described herein have structures to facilitate the use of additional surgical instruments such that the placement of negative pressure device permit the surgeon to advantageously manipulate the other instruments during surgery. The negative pressure is preferably imposed through a plurality of ports which may be disposed in a substantially planar surface of the instrument which contacts the cardiac tissue.

29 Claims, 7 Drawing Sheets

U.S. PATENT DOCUMENTS

| | | | |
|---|---|---|---|
| 810,675 A | 1/1906 | Richter |
| 820,721 A | 5/1906 | Kohlbach |
| 930,236 A | 8/1909 | Schacht |
| 1,202,698 A | 10/1916 | Ford |
| 1,706,500 A | 3/1929 | Smith |
| 2,082,782 A | 6/1937 | Allen |
| 2,233,561 A | 3/1941 | Kalle |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,096,962 A | 7/1963 | Meijs |
| 3,361,133 A | 1/1968 | Kimberly et al. |
| 3,392,722 A | 7/1968 | Jorgensen |
| 3,466,079 A | 9/1969 | Mammel |
| 3,584,822 A | 6/1971 | Oram |
| 3,680,546 A | 8/1972 | Asrican |
| 3,683,926 A | 8/1972 | Suzuki |
| 3,720,433 A | 3/1973 | Rosfelder |
| 3,782,387 A * | 1/1974 | Falabella .................. 128/898 |
| 3,783,873 A | 1/1974 | Jacobs |
| 3,807,393 A | 4/1974 | McDonald |
| 3,807,406 A | 4/1974 | Rafferty et al. |
| 3,858,926 A | 1/1975 | Ottenhues |
| 3,882,855 A | 5/1975 | Shulte et al. |
| 3,912,317 A | 10/1975 | Ohnaka et al. |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,052,980 A | 10/1977 | Grams et al. |
| 4,094,484 A | 6/1978 | Galione et al. |
| 4,096,853 A | 6/1978 | Weigand |
| 4,096,864 A | 6/1978 | Kletschka et al. |
| 4,185,636 A | 1/1980 | Gabbay et al. |
| 4,217,890 A | 8/1980 | Owens |
| 4,226,228 A | 10/1980 | Shin et al. |
| 4,230,119 A | 10/1980 | Blum |
| 4,300,541 A | 11/1981 | Burgin |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,582,353 A * | 4/1986 | Alvernhe .................. 294/64.1 |
| 4,597,382 A | 7/1986 | Perez, Jr. |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,708,510 A | 11/1987 | McConnell et al. |
| D293,470 S | 12/1987 | Adler |
| 4,718,418 A | 1/1988 | L'Esperance, Jr. |
| 4,724,838 A | 2/1988 | Hasson |
| 4,726,356 A | 2/1988 | Santilli et al. |
| 4,726,358 A | 2/1988 | Brady |
| 4,736,749 A | 4/1988 | Lundback |
| 4,747,394 A | 5/1988 | Watanabe |
| 4,747,395 A | 5/1988 | Brief |
| 4,754,746 A | 7/1988 | Cox |
| 4,767,142 A * | 8/1988 | Takahashi et al. ......... 294/64.1 |
| 4,787,662 A | 11/1988 | Dewez |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,925,443 A | 5/1990 | Heilman et al. |
| 4,931,341 A | 6/1990 | Haffer et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,983,093 A * | 1/1991 | Foulke et al. .......... 414/416.08 |
| 4,989,587 A | 2/1991 | Farley |
| 4,991,566 A | 2/1991 | Shulman et al. |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,098,432 A | 3/1992 | Wagenknecht et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,192,070 A | 3/1993 | Nagai et al. |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,290,082 A * | 3/1994 | Palmer et al. ............. 294/64.1 |
| 5,290,227 A | 3/1994 | Pasque |
| 5,293,863 A | 3/1994 | Zhu et al. |
| 5,300,087 A | 4/1994 | Knoepfler |
| 5,306,234 A | 4/1994 | Johnson |
| 5,309,896 A | 5/1994 | Moll et al. |
| 5,318,013 A | 6/1994 | Wilk |
| 5,336,252 A | 8/1994 | Cohen |
| 5,337,754 A | 8/1994 | Heaven et al. |
| 5,339,801 A | 8/1994 | Poloyko et al. |
| 5,345,935 A | 9/1994 | Hirsch et al. |
| 5,348,259 A | 9/1994 | Blanco et al. |
| 5,363,841 A | 11/1994 | Coker |
| 5,363,882 A | 11/1994 | Chikama |
| 5,370,685 A | 12/1994 | Stevens |
| 5,375,588 A | 12/1994 | Yoon |
| 5,381,788 A | 1/1995 | Matula et al. |

| | | | | | | |
|---|---|---|---|---|---|---|
| 5,382,756 A | 1/1995 | Dagan | | 5,891,017 A | 4/1999 | Swindle et al. |
| 5,383,840 A | 1/1995 | Heilman et al. | | 5,894,843 A | 4/1999 | Benetti et al. |
| 5,417,709 A | 5/1995 | Slater | | 5,904,711 A * | 5/1999 | Flom et al. .................. 607/129 |
| 5,425,705 A | 6/1995 | Evard et al. | | 5,906,607 A | 5/1999 | Taylor et al. |
| 5,433,700 A | 7/1995 | Peters | | 5,921,979 A | 7/1999 | Kovacs et al. |
| 5,437,651 A | 8/1995 | Todd et al. | | 5,927,284 A | 7/1999 | Borst et al. |
| 5,452,733 A | 9/1995 | Sterman et al. | | 5,947,896 A | 9/1999 | Sherts et al. |
| 5,453,078 A | 9/1995 | Valentine et al. | | 5,957,832 A | 9/1999 | Taylor et al. |
| 5,467,763 A | 11/1995 | McMahon et al. | | 5,961,481 A | 10/1999 | Sterman et al. |
| 5,480,425 A | 1/1996 | Ogilive | | 5,976,080 A | 11/1999 | Farascioni et al. |
| 5,484,391 A | 1/1996 | Buckman, Jr. et al. | | 5,976,171 A | 11/1999 | Taylor et al. |
| 5,498,256 A | 3/1996 | Furnish | | 6,010,531 A | 1/2000 | Donlon et al. |
| 5,503,617 A | 4/1996 | Jako | | 6,015,378 A | 1/2000 | Borst et al. |
| 5,509,890 A | 4/1996 | Kazama | | 6,029,671 A | 2/2000 | Stevens et al. |
| 5,512,037 A | 4/1996 | Russell et al. | | 6,032,672 A | 3/2000 | Taylor |
| 5,513,827 A | 5/1996 | Michelson | | 6,042,539 A | 3/2000 | Harper et al. |
| 5,514,075 A | 5/1996 | Moll et al. | | 6,110,187 A | 8/2000 | Donlon |
| 5,514,076 A | 5/1996 | Ley | | 6,132,370 A | 10/2000 | Furnish et al. |
| 5,520,609 A | 5/1996 | Moll et al. | | 6,139,492 A | 10/2000 | Vierra et al. |
| 5,520,610 A | 5/1996 | Giglio et al. | | 6,149,583 A | 11/2000 | Vierra et al. |
| 5,522,819 A | 6/1996 | Graves et al. | | 6,183,486 B1 | 2/2001 | Snow et al. |
| 5,529,571 A | 6/1996 | Daniel | | 6,210,323 B1 | 4/2001 | Gilhuly et al. |
| 5,536,251 A | 7/1996 | Evard et al. | | 6,213,940 B1 | 4/2001 | Sherts et al. |
| 5,547,458 A | 8/1996 | Ortiz et al. | | 6,231,585 B1 | 5/2001 | Takahashi et al. |
| 5,549,340 A * | 8/1996 | Nagai et al. ................ 294/64.1 | | 6,251,065 B1 | 6/2001 | Kochamba |
| RE35,352 E | 10/1996 | Peters | | 6,264,605 B1 | 7/2001 | Scirica et al. |
| 5,564,682 A | 10/1996 | Tsuji | | 6,315,717 B1 | 11/2001 | Benetti et al. |
| 5,569,274 A | 10/1996 | Rapacki et al. | | 6,328,688 B1 | 12/2001 | Borst et al. |
| 5,571,074 A | 11/1996 | Buckman, Jr. et al. | | 6,334,843 B1 | 1/2002 | Borst et al. |
| 5,571,215 A | 11/1996 | Sterman et al. | | 6,336,898 B1 | 1/2002 | Borst et al. |
| 5,573,496 A | 11/1996 | McPherson et al. | | 6,346,077 B1 | 2/2002 | Taylor et al. |
| 5,578,061 A | 11/1996 | Stroetmann et al. | | 6,350,229 B1 | 2/2002 | Borst et al. |
| 5,582,580 A * | 12/1996 | Buckman et al. ............. 601/41 | | 6,364,826 B1 | 4/2002 | Borst et al. |
| 5,584,803 A | 12/1996 | Stevens et al. | | 6,371,906 B1 | 4/2002 | Borst et al. |
| 5,607,421 A * | 3/1997 | Jeevanandam et al. ....... 606/15 | | 6,371,910 B1 | 4/2002 | Zwart et al. |
| 5,607,446 A | 3/1997 | Beehler et al. | | 6,375,611 B1 | 4/2002 | Voss et al. |
| 5,613,937 A | 3/1997 | Garrison et al. | | 6,394,948 B1 | 5/2002 | Borst et al. |
| 5,613,950 A | 3/1997 | Yoon | | 6,394,951 B1 | 5/2002 | Taylor et al. |
| 5,632,746 A | 5/1997 | Middleman et al. | | 6,398,726 B1 | 6/2002 | Romans et al. |
| 5,651,378 A | 7/1997 | Metheny et al. | | 6,406,424 B1 | 6/2002 | Williamson et al. |
| 5,662,300 A | 9/1997 | Michelson | | 6,447,443 B1 | 9/2002 | Keogh et al. |
| 5,667,480 A | 9/1997 | Knight et al. | | 6,458,079 B1 | 10/2002 | Cohn et al. |
| 5,707,362 A | 1/1998 | Yoon | | 6,464,629 B1 | 10/2002 | Boone et al. |
| 5,713,951 A | 2/1998 | Garrison et al. | | 6,464,630 B1 | 10/2002 | Borst et al. |
| 5,722,935 A | 3/1998 | Christian | | 6,468,265 B1 | 10/2002 | Evans et al. |
| 5,727,569 A | 3/1998 | Benetti et al. | | 6,478,029 B1 | 11/2002 | Boyd et al. |
| 5,728,151 A | 3/1998 | Garrison et al. | | 6,478,729 B1 | 11/2002 | Rogers et al. |
| 5,730,757 A | 3/1998 | Benetti et al. | | 6,482,151 B1 | 11/2002 | Vierra et al. |
| 5,735,290 A | 4/1998 | Sterman et al. | | 6,494,211 B1 | 12/2002 | Boyd et al. |
| 5,749,892 A | 5/1998 | Vierra et al. | | 6,503,245 B2 | 1/2003 | Palmer et al. |
| 5,755,660 A | 5/1998 | Tyagi | | 6,506,149 B2 | 1/2003 | Peng et al. |
| 5,755,682 A | 5/1998 | Knudson | | 6,537,212 B2 | 3/2003 | Sherts et al. |
| 5,766,151 A | 6/1998 | Valley et al. | | 6,565,508 B2 | 5/2003 | Scirica et al. |
| 5,772,583 A | 6/1998 | Wright et al. | | 6,589,166 B2 | 7/2003 | Knight et al. |
| 5,782,746 A | 7/1998 | Wright | | 6,592,573 B2 | 7/2003 | Castaneda et al. |
| 5,782,813 A | 7/1998 | Yoon | | 6,607,479 B1 | 8/2003 | Kochamba et al. |
| 5,795,291 A | 8/1998 | Koros et al. | | 6,610,008 B1 | 8/2003 | Spence et al. |
| 5,797,934 A * | 8/1998 | Rygaard ..................... 606/153 | | 6,610,009 B2 | 8/2003 | Person et al. |
| 5,797,960 A | 8/1998 | Stevens et al. | | | | |
| 5,799,661 A | 9/1998 | Boyd et al. | | FOREIGN PATENT DOCUMENTS | | |
| 5,803,902 A | 9/1998 | Sienkiewicz et al. | | | | |
| 5,807,243 A | 9/1998 | Vierra et al. | | DE | 9004513 | 6/1990 |
| 5,813,410 A | 9/1998 | Levin | | DE | 41 39 695 A1 | 6/1993 |
| 5,818,231 A | 10/1998 | Smith | | EP | 0 293 760 A2 | 12/1988 |
| 5,820,555 A | 10/1998 | Watkins et al. | | EP | 0 293 760 A3 | 12/1988 |
| 5,836,311 A | 11/1998 | Borst et al. | | EP | 0 293 760 B1 | 12/1988 |
| 5,846,187 A | 12/1998 | Wells et al. | | EP | 0 630 629 A1 | 5/1994 |
| 5,864,275 A | 1/1999 | Ohashi et al. | | EP | 0 668 058 A1 | 8/1995 |
| 5,871,489 A | 2/1999 | Ovil | | EP | 0 803 228 A1 | 10/1997 |
| 5,875,782 A | 3/1999 | Ferrari et al. | | EP | 0 808 606 A1 | 11/1997 |
| 5,882,345 A | 3/1999 | Yoon | | GB | 473.451 | 1/1915 |
| 5,885,272 A * | 3/1999 | Aita et al. ..................... 606/7 | | GB | 168216 | 9/1921 |
| 5,888,247 A | 3/1999 | Benetti | | GB | 2 233 561 A | 1/1991 |

| | | |
|---|---|---|
| GB | 2 267 827 A | 12/1993 |
| SU | 938967 | 7/1982 |
| WO | WO 87/04081 | 7/1987 |
| WO | WO 88/00481 | 1/1988 |
| WO | WO 92/21293 | 12/1992 |
| WO | WO 93/09720 | 5/1993 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/32882 | 10/1996 |
| WO | WO 96/40354 | 12/1996 |
| WO | WO 97/10753 | 3/1997 |
| WO | WO 97/26828 | 7/1997 |
| WO | WO 97/32514 | 9/1997 |
| WO | WO 97/40738 | 11/1997 |
| WO | WO 97/40752 | 11/1997 |
| WO | WO 98/17182 | 4/1998 |
| WO | WO 98/27869 | 7/1998 |

OTHER PUBLICATIONS

Ancalmo, et al. "A modified sternal retractor," *Ann. Thorac, Surg.*, (1976) vol. 21: 174.

Angelini, et al. "A fiber-optic retractor for harvesting the internal mammary artery," *Ann. Thorac. Surg.*, (1990) vol. 50: 314-315.

Angelini, et al. "A simple, inexpensive method of heart retraction during coronary artery bypass surgery," *Ann. Thora. Surg.*, (1988) vol. 46: 46-247.

Ankeney, et al. "To use or not to use the pump oxygenator in coronary bypass operations," *The Annals of Thoracic Surgery*, (1975) vol. 19(1): 108-109.

Anstadt, et al. "Direct mechanical ventricular actuation for cardiac arrest in humans," *Chest*, (1991) vol. 100(1): 86-92.

Antinori, et al. "A method of retraction during reoperative coronary operations using the favaloro retractor," *The Society of Thoracic Surgeons*, (1989).

Archer, et al. "Coronary artery revascularization without cardiopulmonary bypass," *Texas Heart Institute Journal*, (1984) vol. 11(1): 52-57.

Arom, et al. "Mini-sternotomy for coronary artery bypass grafting," *The Annals of Thoracic Surgery*, (1996) vol. 61: 1271-1272.

Ballantyne, et al. "Delayed recovery of severely 'stunned' myocardium with the support of a left ventricular assist device after coronary artery bypass graft surgery," *Journal of the American College of Cardiology*, (1987) vol. 10(3): 710-712.

Bedellino, et al. "The cardiac rag—Simple exposure of the heart," *Texas Heart Institute Journal*, (1988) vol. 15(2): 134-135.

Beg, et al. "Internal mammary retractor," *Ann Thorac, Surg.*, (1985) vol. 39(1): 286-287.

Benetti, et al. "Direct coronary surgery with saphenous vein bypass without either cardiopulmonary bypass graft or cardiac arrest," *The Journal of Cardiovascular Surgery*, (1985) vol. 26(3): 217-222.

Benetti, et al. "Direct myocardial revascularization without extracorporeal circulation," *Chest*, (1991) vol. 100(2): 312-316.

Benetti. "Coronary revascularization with arterial conduits via a small thoracotomy and assisted by thoracoscopy, although without cardiopulmonary bypass," *Cor Europaeum*, (1995) vol. 4(1): 22-24.

Borst, et al. "Regional cardiac wall immunobilization for open chest and closed Chest coronary artery bypass grafting on the beating heart: The 'octopus' method," *Circulation*, (1995) vol. 92(8 supp. I): I-177.

Borst, et al. "Coronary artery bypass grafting without cardiopulmonary bypass and without interruption of native coronary flow using a novel anastomosis site restraining device (octopus)", *J Am. Coll. Cardiol.*, (1996) vol. 27(6): 1356-1364.

Bugge . "A new internal mammary artery retractor," *Thorac. Cardiovasc Surgeon*, (1990) vol. 38: 316-317.

Buffolo, et al. "Direct myocardial revascularization without cardiopulmonary bypass," *Thorac. Cardiovasc. Surgeon*, (1985) vol. 33: 26-29.

Calafiore, et al. "Minimally invasive coronary artery bypass grafting," *The Annals of Thoracic Surgery*, (1996) vol. 62: 1545-1548.

Calvin, et al. "Circumflex exposure using a cardiac sling," *Ann Thorac Surg*, (1990_ vol. 49: 833-834.

Campalani, et al. "A new self-retaining internal mammary artery retractor," *J. Cardiovas. Surg.*, (1987) vol. 28: 347-348.

Chaux, et al. "A new concept in sternal retraction: Applications for internal mammory artery dissection and valve replacement surgery," *Ann. Thorac. Surg.*, (1986) vol. 42: 473-474.

Cohen, et al. "Mini-sternotomy for coronary artery bypass grafting," *The Annals of Thoracic Surgery*, (1996) vol. 62: 1884-1885.

Cutler, et al. "New use for an old clamp," *Archives of Surgery*, (1980) vol. 115: 1136-1137.

Delacroix-Chevalier. "Surgical instruments", *IMA Saving Packages Brochure*.

Delrossi, et al. "A new retractor to aid in coronary artery surgery," *The Annals of Thoracic Surgery*, (1983) vol. 36(1): 101-102.

Fanning, et al. "Reoperative coronary artery bypass grafting without cardiopulmonary bypass," *The Annals of Thoracic Surgery*, (1993) vol. 55(2): 486-489.

Favaloro, et al. "Direct myocardial revascularization by saphenous vein graft," *The Annals of Thoracic Surgery*, (1970) vol. 10(2): 97-111.

Fonger, et al. "Enhanced preservation of acutely ischmenic myocardium with transeptal left ventricular assist," *The Annals of Thoracic Surgery*, (1994) vol. 57(3): 570-575.

Gacioch, et al. "Cardiogenic shock complicating acute myocardial infarction: The use of coronary angioplasty and the integration of the new support device into patient management," *Journal of the American College of Cardiology*, (1992) vol. 19(3).

Green. "Technique of internal mammary-coronary artery anastomosis," *The Journal of Cardiovascular Surgery*, (1979) vol. 78: 455-479.

Guzman. "Transient radial nerve injury related to the use of a self retraining retractor for internal mammary artery dissection," *J. Cardiovasc. Surg.*, (1989) vol. 30: 1015-1016.

Hasan, et al. "Technique of dissecting the internal mammary after using the moussalli bar," *European Journal of Cardio Thoracic Surgery*, (1990) vol. 4: 571-572.

Itoh, et al. "New modification of a mammory artery retractor," *Ann. Thorac. Surg.*, (1994) vol. 57:1670-1671.

*Japanese Journal of Thoracic Surgery*, (1989) vol. 42(2).

Japanese Article "Heart Retractor".

Janke. "Heart support for coronary bypass surgery involving the circumflex artery system," *The Journal of Thoracic and Cardiovascular Surgery*, pp. 883-884.

Kolessov. "Mammary artery-coronary artery anastomosis as method of treatment for angina pectoris," *Thoracic and Cardiovascular Surgery*, (1967) vol. 54(4): 535-544.

Kazama, et al. "Fabric heart retractor for coronary artery bypass operations," *The Annals of Thoracic Surgery*, (1993) vol. 55: 1582-1583.

Kresh, et al. "Heart-mechanical assist device interaction," *Trans. Am. Soc. Artif. Intern. Organs*, (1986) vol. 32: 437-443.

Lavergne, et al. "Transcatheter radiofrequency ablation of atrial tissue using a suction catheter," *PACE*, (1989) vol. 12(Part II): 177-186.

Lonn, et al. "Coronary artery operation supported by the hemopump: An experimetnal study on pigs," *The Annals of Thoracic Surgery*, (1994) vol. 58(1): 516-523.

Matsuura, et al. "A new device for exposing the cirumflex coronary artery," *The Annals of Thoracic Surgery*, (1995) vol. 59: 1249-1250.

McGee, et al. "Extended clinical support with an implantable left ventricular assist device," *Trans. Am. Soc. Artif. Intern. Organs*. (1989) vol. 35: 614-616.

McKeown, et al. "A modified sternal retractor for exposure of the internal mammary artery," *Ann. Thorac. Surg.*, (1981) vol. 32: 619.

Ochsner, et al. "Surgical management of diseased intracavitary coronary arteries," *The Annals of Thoracic Surgery*, (1984) vol. 38(4): 356-362.

Parsonnet, et al. "Graduated probes for coronary bypass surgery," *The Journal of Thoracic and Cardiovascular Surgery*, (1974) vol. 68(3): 424-426.

Parsonnet, et al. "Self—retaining epicardial retractor for aortocoronary bypass surgery," *The Journal of Thoracic and Cardiovascular Surgery*, (1979): 629-630.

Pfister, et al. "Coronary artery bypass without cardiopulmonary bypass," *The Annals of Thoracic Surgery*, (1992) vol. 54(6): 1085-1092.

Phillips, et al. "A versatile retractor for use in harvesting the internal mammary artery and performing standard cardiac operations," *J. Thorac. Cardiovasc. Surg.*, (1989) vol. 97: 633-635.

"Pilling surgical instruments", A *Rusch International Company Brochure*.

Pittman, et al. "Improved visualization of the internal mammary artery with a new retractor system," *Ann. Thorac. Surg.*, (1989) vol. 48: 869-870.

Riahi, et al. "A simple technique and device to provide a bloodless operative field in coronary artery surgery without cross-clamping the aorta," *The Journal of Thoracic and Cardiovascular Surgery*, (1973) vol. 66(6): 974-978.

Richenbacher, et al. "Current status of cardiac surgery: A 40-year review," *Journal of American College of Cardiology*, vol. 14(3): 535-544.

Robicsek. "Aortic spoon-jaw clamp for aorto-saphenous vein anastomosis," *J. Card. Surg.*, (1995) vol. 10: 583-585.

Robinson, et al. "A minimally invasive surgical method for coronary revascularization—Preliminary experience in five patients," *Circulation*, (1995) vol. 92(8): 1-176.

Rousou, et al. "Cardiac retractor for coronary bypass operations," *Ann Thorac. Surg.*, (1991) vol. 52: 877-878.

Roux, et al. "New helper instrument in cardiac surgery", *Ann. Thoracic Surgery*, (1989) vol. 48: 595-596.

Roux, et al. "Internal mammary artery dissection: A three dimensional sternal retractor," *J. Cardiovasc. Surg.*, vol. 30: 996-997.

Ruzevich, et al. "Long-term follow-up of survivors of postcardiotomy circulatory support," *Trans. Am. Soc. Artif. Intern. Organs*, (1988) vol. 34: 116-124.

Scholz, et al. "Transfemoral placement of the left ventricular assist device 'hemopump' during mechanical resuscitation," *Thoracic and Cardiovascular Surgeon*, (1990) vol. 38: 69-72.

Splittgerber, et al. "Exposing the circumflex coronary artery: The heartflip technique," *Ann Thorac Surg.*, (1996) vol. 61: 1019-1020.

Stevens, et al. "Closed chest coronary artery bypass with cardioplegic arrest in the dog," $67^{th}$ *Scientific Session*, 238, I-251.

Trapp, et al. "Placement of coronary artery bypass graft without pump oxygenator," *J. of the Society of Thoracic Surgeons and The Southern Thoracic Surgeons Assn.*, (1975) vol. 19(1).

USSC Cardiovascular Thora-Lift™, United States Surgical Corporation, Norwalk, Connecticut, Product Brochure.

Vincent. "A compact single post internal mammary artery dissection retractor," *Eur. J. Cardio-Thor. Surg.*, (1989) vol. 3: 276-277.

Westaby. "Coronary surgery without cardiopulmonary bypass," *British Heart Journal*, (1995) vol. 73: 203-205.

Westaby, et al. "Less invasive coronary surgery: Consensus from the oxford meeting," The *Annals of Thoracic Surgery*, (1996) vol. 62: 924-931.

Zumbro, et al. "A prospective evaluation of the pulsatile assist device," *The Annals of Thoracic Surgery*, (1979) vol. 28(2): 269-273.

* cited by examiner

SURGICAL DEVICES FOR IMPOSING A NEGATIVE PRESSURE TO STABILIZE THE CARDIAC TISSUE DURING SURGERY

The present application is a continuation of application Ser. No. 09/440,106, filed Nov. 15, 1999 now U.S. Pat. No. 6,852,075 and titled "*Surgical Devices for Imposing a Negative Pressure To Stabilize Cardiac Tissue During Surgery*," pending, which is a divisional of application Ser. No. 08/870,687, filed Jun. 6, 1997, now U.S. Pat. No. 6,032,672, which is a divisional of application Ser. No. 08/603,328, filed Feb. 20, 1996, now U.S. Pat. No. 5,727,569, each of which are hereby incorporated by reference thereto, in their entireties.

Surgeries to treat disease in the heart, particularly blockages in coronary vessels, are becoming increasingly common and necessary to treat atherosclerosis and other conditions causing reduced blood flow to the heart. For many years, surgeons have performed "open-heart" surgery to repair defects in the heart and the associated cardiovascular system. As these procedures have become more common and more costly, a need has developed for techniques to make cardiac surgical procedures less traumatic to the patient. The necessity of attaching a surgical patient to a cardiopulmonary bypass (CPB) apparatus is a primary contribution to the trauma inherent in traditional procedures. To attempt to alleviate the trauma and side effects of CPB, surgeons have begun performing cardiac surgeries without stopping the heart. To successfully perform such surgery, several challenges must be met. One particular problem confronting the surgeon who operates on the beating heart is the difficulty in performing extremely delicate surgical procedures while the contractions of the heart muscles cause the surface of the heart to continuously move.

To attempt to restrict the motion of heart at the particular area where the surgeon is working, the surgeon may pass at least a pair of sutures through the exterior tissue layers of the heart. By pulling the sutures in opposite directions, the tissue is stretched, and the motion caused by the contractions of the heart muscles is reduced or partially compensated. This technique is not completely effective in preventing the natural motion of the heart and requires extra time to place the sutures, and, additionally, may cause damage to the cardiac tissue when the sutures are placed or manipulated. Preferably, the surgeon would be able to fix the motion of the cardiac tissue containing or adjacent to an area where surgery is to be performed without the need to attach or manipulate additional sutures. The ability to fix the position of the cardiac tissue in a region of the heart would permit the surgeon to perform delicate surgical procedures on the beating heart while the portion of the heart on which the surgery is performed remains substantially motionless throughout the procedure.

SUMMARY OF THE INVENTION

This invention is devices and techniques which use a negative pressure (vacuum) applied through a surgical instrument, to fix the position of a portion of the surface of a beating heart so that a surgical procedure can be more easily performed. The devices disclosed herein apply a negative pressure at several points on the outer surface of the heart such that a portion of the exterior tissue of the heart is fixed in place by the suction imposed through the surgical instrument. Because the negative pressure introduced through the instrument -s the position of a region of tissue, the instrument remains at a constant distance from the particular portion of the heart where the surgery is being performed. In this configuration, the device may also serve as a support or platform so that other surgical instruments or devices can be advantageously used at the site. In certain preferred embodiments, the devices described herein have structures to facilitate the use of additional surgical instruments such that the placement of the negative pressure instrument permits the surgeon to advantageously manipulate the other instruments used during the surgery.

The negative pressure is preferably imposed through a plurality of ports which may be disposed in a substantially planar surface of the instrument which contacts the cardiac tissue. The ports are preferably oriented such that the pressure is applied at several points over the target area to fix the position of the tissue and to reduce any trauma to the tissue caused by the negative pressure.

DETAILED DESCRIPTION OF THE INVENTION

Figure 1:
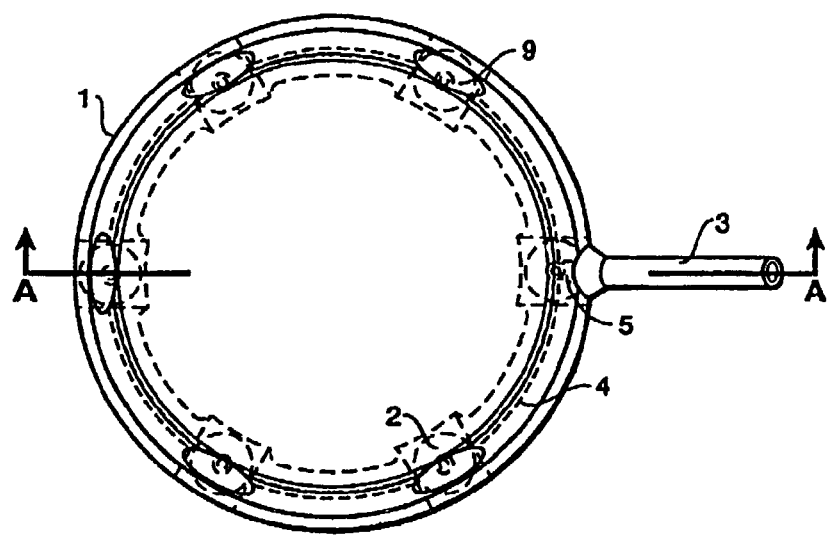
FIG. 1 is an embodiment of the invention having a substantially annular housing with a plurality of suction ports disposed about the periphery of the instrument and having openings in the bottom surface which contacts the heart.

This invention is surgical instruments and techniques which advantageously apply a negative pressure to the surface of the heart so that a portion thereof is maintained at a fixed position during a surgical procedure. The negative pressure is introduced to the instrument and is applied at several points over the surface of the heart proximate to or surrounding the portion of the heart whose position is desired to be fixed during the procedure. The instruments feature several suction ports which are brought into contact with the heart, followed by the application of a negative pressure through the instruments, to fix the position of the tissue based on the placement of the instrument. The Instruments may also contain a sealed, airtight, pressure conducting chamber for operably connecting to a pressure inlet for communicating the negative pressure to the suction parts. Alternatively, each suction port may have a dedicated vacuum line attached thereto.

The shape of the instrument may be varied depending on the particular application or the clinical diagnosis for an individual patient. In some embodiments, the shape of the instrument is defined by a housing forming a complete or partial, substantially annular, ring having the suction ports disposed about the periphery of the bottom surface of the housing. The suction ports are contained within the base of the instrument and the opening of the suction ports are contained in the bottom surface of the instrument which may be substantially planar or may be shaped to conform to the surface of the heart.

In another embodiment, the operative portion of the instrument may be defined by one or more arrays of suction ports which are substantially linear. The suction ports may be contained in a block which has at least one vacuum line attached thereto. This design is particularly suitable for an instrument having a shaft affixed thereto for positioning the block containing the suction ports. The shaft may be fixed to a rigid support during the procedure or may be part of a hand-held instrument having a handle structure adapted to be grasped by the human hand. In a preferred embodiment, the hand-held instrument contains a pair of shafts having a block and suction port assembly at each end thereof. The shafts are connected at an intermediate portion by a pivot which allows the suction port assemblies to move relative to one another, to be oriented and manipulated by hand, and to be locked into place in a desired configuration.

An embodiment having more than one movable member in which suction ports are contained offers the advantage that a negative pressure may be first imposed through the suction ports of each movable member to fix the tissue, followed by manipulation of the individual members which causes the tissue to be stretched or oriented such that one portion of the cardiac tissue is fixed in position by one movable member and can be oriented relative to another portion fixed by a second movable member.

The negative or vacuum pressure imposed may be varied depending on the design of the instrument, the orientation of the ports, and the amount of pressure needed to hold a particular region of the heart in place. When manipulating the instruments of this invention, it is not, desired to exert a downward force on the instrument once the instrument engages the cardiac tissue because the tissue could be damaged by being drawn into the suction ports, thus risking interruption of blood flow and ischemic or reperfusion injury to the cardiac tissue. However, once a negative pressure is imposed, the instrument may be drawn away from the heart such that the portion of the surface tissue fixed by the suction ports is slightly elevated relative to the remainder of the heart.

Figure 3:
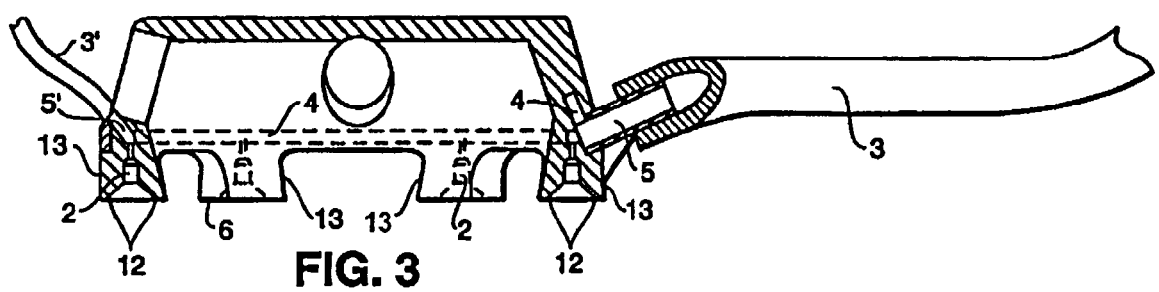
FIG. 3 is a section of a substantially circular embodiment showing a preferred configuration for the suction ports and a pressure conducting chamber for introducing the negative pressure to each suction port.

Referring to FIGS. 1 and 3, an embodiment of the invention is an instrument comprised of an annular housing 1 which could have an alternate shape depending on the design and clinical application of the instrument. For example, the body of the instrument has a housing which may be a portion of a circle, an oval, semi-oval, U-shape, or linear member.

The portion of the housing 1 which contains the suction ports 2 has a bottom surface 6 which rests against the surface of the heart and therefore should be substantially planar or curved to the extent necessary to simultaneously bring the suction ports 2 into conforming contact with the heart. Referring to FIGS. 1 and 3, one embodiment of the invention has suction ports 2 equally spaced about the circumference of the housing 1. For purposes of stability, it is preferred that each suction port 2 be substantially equidistant from each adjacent port and spread over the entire portion of the instrument at the points of contact to the heart so that the instrument is more stably affixed to the surface of the heart when a negative pressure is imposed. As described in detail below, the housing 1 may also have one or more instrument ports 9 to facilitate introducing a surgical instrument to the site of the surgery to function on or in proximity to the fixed portion of the cardiac tissue.

The interior of the housing 1 may be further comprised of a means for introducing a negative pressure to the suction ports 2. For example, each suction port 2 may have a dedicated vacuum line 3 for introducing a negative pressure to each suction port 2. However, it is preferred that a single vacuum line 3 introduce the negative pressure via an inlet 5 which leads to an airtight, sealed, and pressure conducting chamber 4 contained within the annular housing 1 which in turn communicates the negative pressure to each suction port 2. Thus, by connecting a negative pressure source to the inlet 5, the negative pressure is introduced to the instrument through inlet 5, thereby creating a negative pressure in the pressure conducting chamber 4 which is communicated to each suction port 2. The housing may also have at least one instrument port 9 comprised of an opening that preferably traverses the width of the housing and is shaped to receive an instrument. In use, the surgeon may advantageously rely on the housing 1 as a platform for other instruments which may advantageously be used at the portion of the heart fixed in place by the negative pressure. The instrument port 9 may be a simple opening in the housing I or may be designed to operably receive a specific instrument as described in more detail below.

In use (See FIG. 4), the instrument is gently positioned on the surface of the heart by manipulating the position of the housing 1 such that each suction port 2 rests against the cardiac tissue. Once the instrument is positioned on the surface of the heart, the negative pressure is applied through vacuum line 3 and inlet 5 while the housing may be gently manipulated to insure that the negative pressure is causing the cardiac tissue to become fixed to each suction port 2. Once the suction ports become functionally attached to the surface of the heart, the portion of the surface of the heart becomes fixed relative to the instrument. Once the negative pressure is applied, the instrument may be attached to a stable support such as a rib retractor or other structure which does not move relative to the beating heart.

Figure 2:
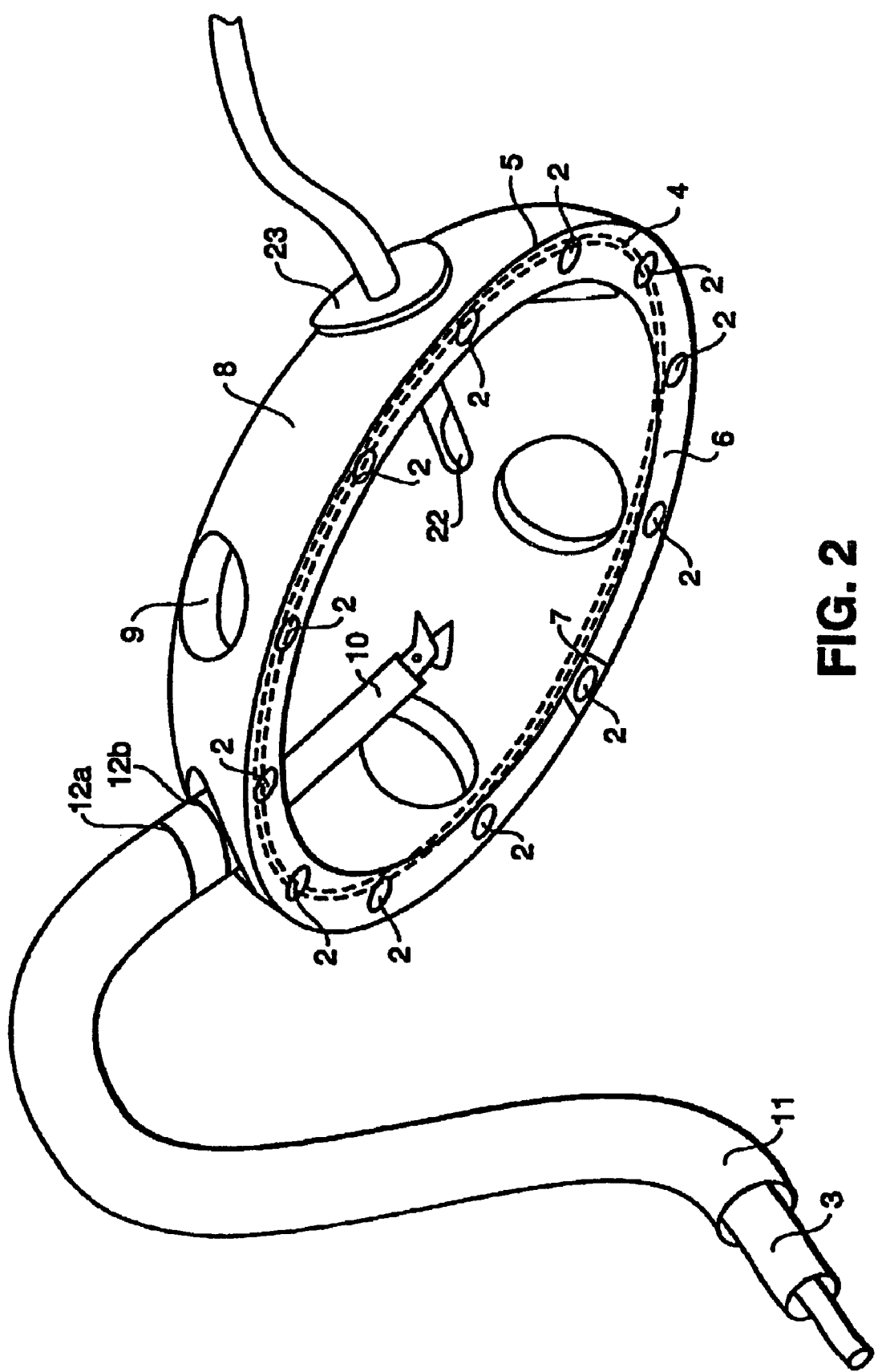
FIG. 2 is a dome-shaped or semi-spherical embodiment having a plurality of suction ports disposed about the periphery of the bottom surface and having several instrument ports in the dome portion through which additional surgical instruments may be introduced, positioned, or manipulated.

Referring to FIG. 2, a dome-shaped or semi-spherical embodiment of the invention has a plurality of suction ports 2 spaced about the periphery of the bottom surface 6 of the dome portion 8 such that the entire instrument is fixed to the cardiac tissue at the point of each of the several suction ports 2. As with the above embodiment, it is preferred that each suction port 2 be pneumatically connected via an air-tight pressure conducting chamber 4. The base of the instrument is comprised of a substantially flat bottom surface 6 wherein the opening of each of the suction ports 2 is flush at the bottom surface 6. The bottom surface 6 is preferably substantially flat because the bottom surface 6 will engage the surface of the heart when the negative pressure is imposed. Alternatively, depending on the size of the instrument and the location of placement on the surface of the heart, the bottom surface 6 may be contoured so that the suction ports 2 may engage a curved surface of the heart. The bottom surface 6 may also have a separate contact layer 7 to cushion the contact between the instrument and the heart tissue and to facilitate forming a tight seal when the negative pressure is imposed. The contact layer 7 may cover substantially the entire bottom surface 6 proximate to the openings of the suction ports 2. If the material surrounds the openings of the suction ports, it is preferable that the material not be air permeable to prevent the negative pressure from passing through the contact layer 7. Also, the contact layer 7 may be attached at the periphery of the bottom surface 6. The available materials for the contact layer 7 include the well-known and commercially available medical plastics such as TEFLON®, silicone, and others which are pliable and biocompatible.

The dome-shaped or semi-spherical embodiment of the invention advantageously has at least one instrument port 9 which may be placed in any of several locations but which is preferably located in the dome portion 8 of the apparatus. The instrument port 9 facilitates introducing the functional portion of an instrument 10 into the interior of the dome portion 8, such that the instrument 10 can perform any of several functions on the cardiac tissue. The instrument 10 could include a cutting apparatus, visual means, such as a scope or light, suturing instruments, suction, blowing, or irrigation apparatus or any like instrument used during a surgical procedure. Multiple instrument ports 9 disposed in the dome portion 8 allow several instruments 10 to be introduced to the surgical site from numerous directions and to be fixed in place relative to the heart.

The instrument ports 9 may be comprised of only a simple opening in the dome portion 8. Alternatively, the instrument ports 9 may also have a flexible or rigid shaft 11 or other attachment means fixed to the dome portion 8 to facilitate introducing an instrument or a member associated therewith such as wires, tubes, cables which comprise or are used to perform the function of the instrument 10. The shaft 11 may also comprise the inlet (not shown) for introducing negative pressure to the pressure conducting chamber 4. Because the dome portion 8 remains at a fixed distance to the heart, the instrument ports 9 or shaft 11 may have a collar 23 or stop associated therewith such that the distance between the instrument 10 and the heart can be predetermined and fixed by, for example, abutting a stop 12a on the instrument 10 against a stop 12b or collar on the instrument port 9.

The instrument ports may also contain a locking means which may be magnetic or suction-driven so that the instrument 10 can be locked into place on the dome-portion 8. For example, the surgeon may view the procedure via a scope 22 which communicates an image to a video monitor. This invention may be advantageously used to establish and maintain an optimal position for the scope by inserting the scope 22 through the instrument port and then fixing the position of the scope 22. The end of the scope 22 may have a collar 23 or other stop mechanism near its end, such that the scope 22 may be introduced through the instrument port 9 wherein the movement of the scope 22 toward the heart is terminated by the contact between the collar 23 of the scope 22 and the periphery of the instrument port 9.

Referring to FIG. 3, a sectional view through line A-A at FIG. 1 shows the interior of the pressure conducting chamber 4 and associated passages or conduits associated with the suction ports 2 such that the negative pressure in the pressure conducting chamber 4 is introduced from vacuum line 3, via inlet 5, and ultimately to the suction ports 2. The suction ports 2 have a substantially circular opening 12 disposed in the bottom surface 6. Although this embodiment has a single inlet 5 such that the pressure is introduced to each suction portion 2 via the pressure conducting chamber 4, one or more of the suction ports 2 may each have an independent inlet 5' for a separate vacuum line 3'.

As noted above, the suction ports 2 are disposed within a bottom surface 6 which is preferably substantially flat. As noted above, the bottom surface 6 of the housing 1 may be a continuous ring or other annular shape which contacts the heart about the entire periphery of housing 1, but may also be comprised of a plurality of individual bases 13 which contain the one or more suction ports 2 and which contact the heart at several independent points which may be co-planar or which may be adapted to the contours of the heart.

Figure 4:
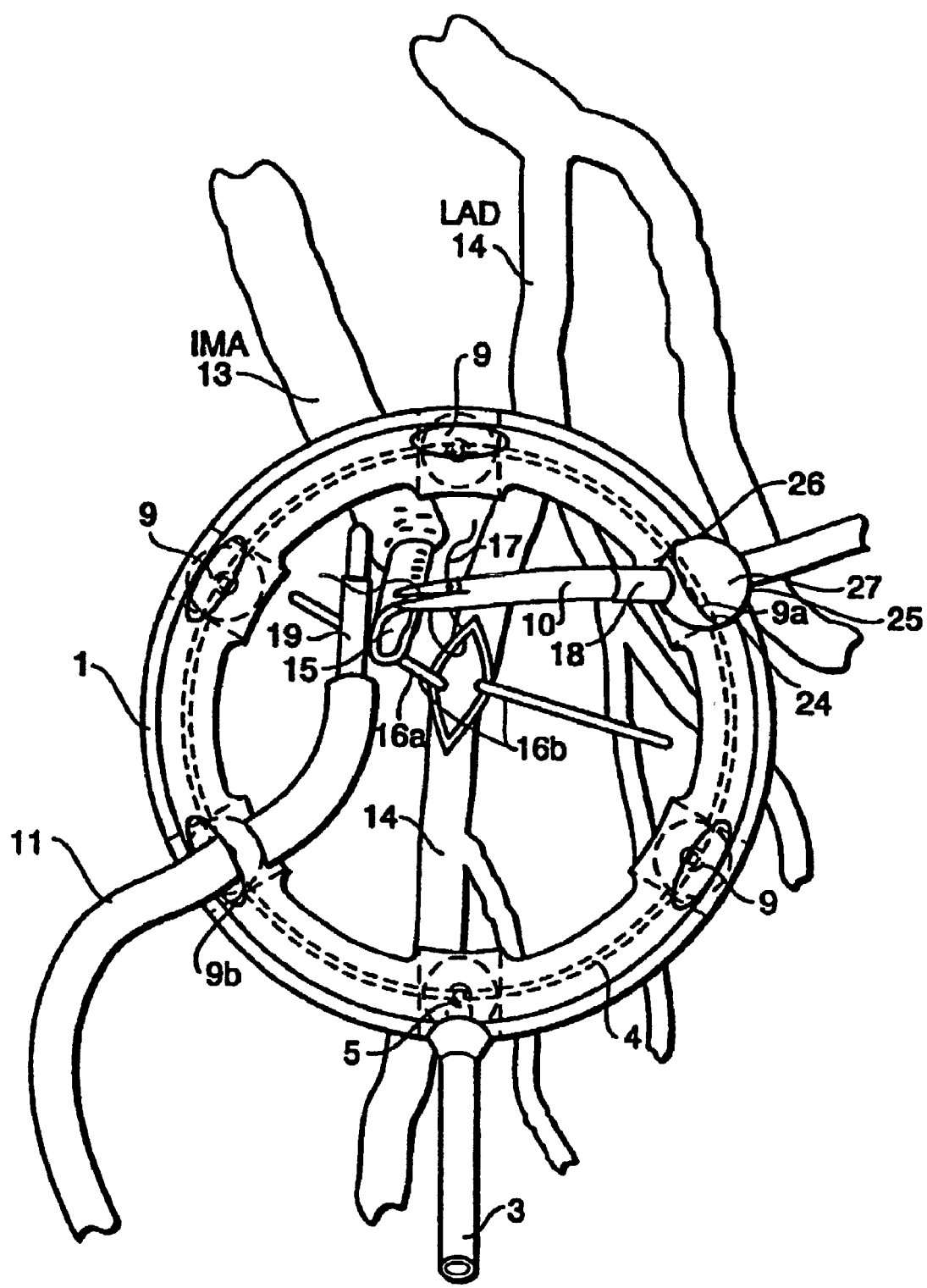
FIG. 4 is an embodiment of the instrument, in use, which is fixed on the surface of the heart and has additional surgical instruments operably associated therewith to facilitate a graft being inserted to form an anastomosis between the internal mammary artery (IMA) and the left anterior descending (LAD) artery.

Referring to FIG. 4, FIG. 4 shows an embodiment of the invention in use in a coronary artery bypass graft (CABG) procedure where an anastomosis is formed between the internal mammary artery IMA 13 and the left anterior descending artery LAD 14 and which is held open by vessel retractors 16a and 16b. One end of the anastomosis is sewn to the LAD 14 by sutures 17 being manipulated by instrument 10. A vacuum line 3 is attached to inlet 5, to introduce a negative pressure to the pressure conducting chamber 4. An instrument 10, which in this example is manipulating suture 17 for sewing the anastomosis at the LAD 14, is introduced via instrument port 9a located in the housing 1 of the apparatus. An instrument port 9a has a shaft 18 disposed within the instrument port 9a to facilitate positioning the instrument 10 relative to both the housing 1 and to the surgical site. The shaft 18 traverses all or a portion of the instrument port 9a and may be flexible such that the shaft 10 can be oriented in a fashion to direct the instrument 10 to the desired point within the surgical field. The shaft 18 may also be incorporated into a pivot 24 of any of several configurations including a ball 25 and socket 26 joint having a passage 27 running axially through the ball 25 wherein the shaft 18 is contained in the passage 27 such that the ball 25 is rotated within the socket 26 to rotate the instrument 10 about the pivot 24 to position the functional end of the instrument 10. An example of another instrument 19 is inserted through instrument port 9b by passing the instrument 19 through a rigid or flexible shaft 12 which is disposed within the instrument port 9b. In this example, the instrument 19 passes through the shaft 12 such that the position of the functional end of the instrument 19 is fixed. In the example shown in FIG. 4, the instrument 19 is being used to grasp the IMA 13 proximate to the attachment of the graft.

Figure 5:
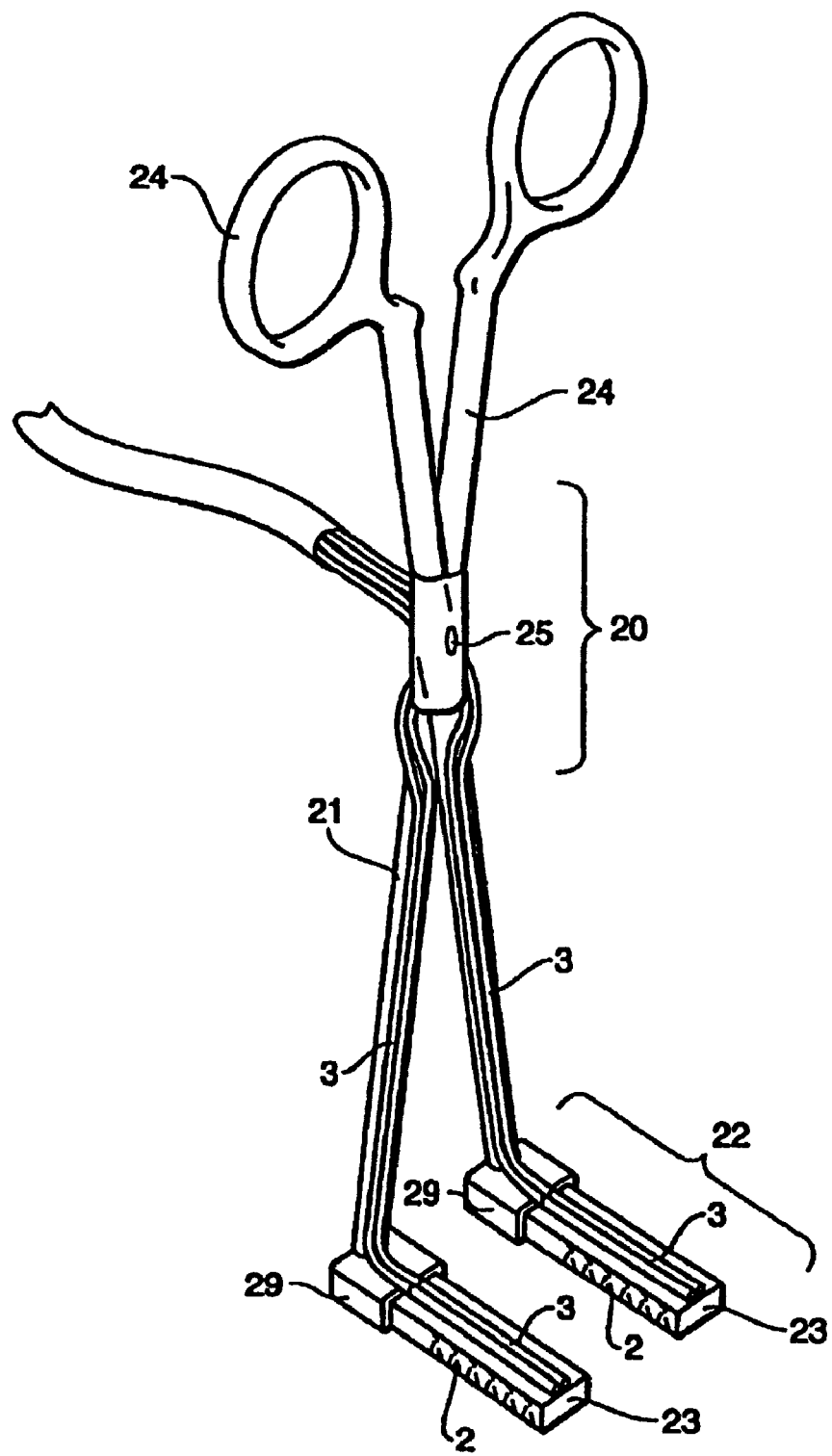
FIG. 5 is an alternative embodiment of the invention wherein the suction ports for imposing the negative pressure are affixed to a shaft which may be part of a hand-held device and are contained in a block where a plurality of individual suction ports are arranged in an array.

Referring to FIG. 5, pursuant to this invention, the suction ports 2 may be incorporated into a hand-held apparatus 20 having a shaft 21 attached to a suction part assembly 22 containing the suction ports 2, at least one vacuum line 3, and a block 23 wherein the suction ports 2 are contained. This embodiment may be operated by a surgeon or surgical assistant by hand grips 24 or the hand grips 24 may be replaced by a conventional attachment (not shown) for fixing the shaft 21 to a stable support such as a surgical retractor or other such fixed structure available during the surgical procedure. In a preferred embodiment, a pair of shafts 21 are interlinked by a pivot link 25 at an intermediate point in the shaft 21 such that each suction port assembly may be positioned independently of one another either before or after the negative pressure is applied. In this configuration, the cardiac tissue which is functionally attached to the instrument at the points of contact with the suction port assembly 22 may be drawn apart by imposing a negative pressure through the suction ports 2 and then manipulating the rigid shafts 21, or hand grips 24 of the instrument 20 such that each suction port assembly 22 is moved a distance from the other. The suction port assembly 22 is comprised of the block 23, in which the suction ports 2 are contained, and a receiving means 29 located at the terminal (lower) end at the shaft 21 which is shaped to receive the block 23 and to pen-nit introduction of the negative pressure from vacuum line 3 to the suction ports 2 contained within the block. The negative pressure is preferably, imposed by one or more vacuum lines 3 which may run parallel to the shaft 21 before terminating in the block 23 containing the suction ports 2 or at any convenient point in the suction port assembly 22. In a preferred embodiment, the blocks 23 are substantially rectangular structures wherein the suction parts 2 are placed in an array as described below.

Figure 6:
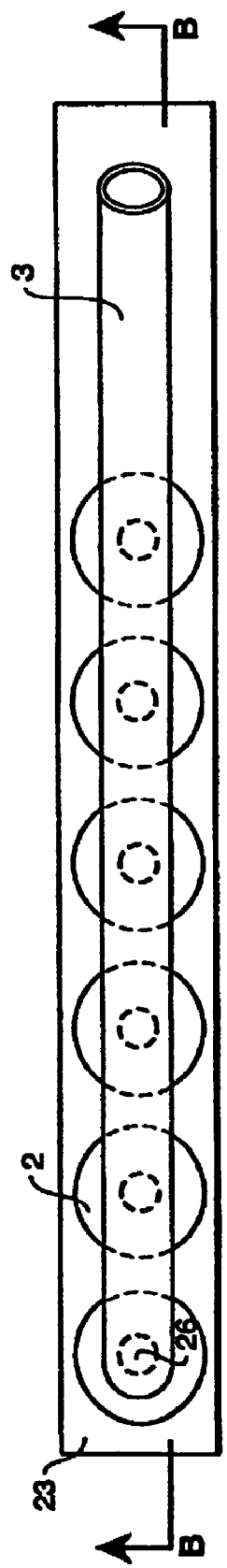
FIG. 6 is a plurality of suction ports contained within a block having attached thereto a pair of vacuum lines for introducing a negative pressure to each suction port.

Referring to FIG. 6, the block 23 is comprised of a plurality of suction ports 2 which are connected to vacuum line 3 to create a negative pressure at each suction port 2. The number of individual vacuum lines 3 may be any number less than or equal to the number of suction ports 2. An individual suction port 2 may be connected to negative pressure via the pressure conducting space 4 (See FIG. 7A) or by a passage 26 which communicates an individual suction port 2 directly to the vacuum line 3. The passage 26 is preferably smaller in circumference than the opening of the suction port 2. In the embodiment of FIG. 6, every other suction port 2 is connected to either of two vacuum lines 3 which traverse substantially the length of the block 23. Alternatively, each suction port may also be connected to a single suction line as shown in FIG. 8. In the embodiment of FIG. 6, the passages 26 are oriented off-center to the circumference of the opening of the suction port 2. In a preferred embodiment, the block 23 is a separate molded rubber unit which is configured to fit reversibly into a receiving means 29 at the terminal end of the shaft 21. In this configuration, the suction port assembly 22 may be disassembled and the block 23 disposed after a single use.

Figure 7:
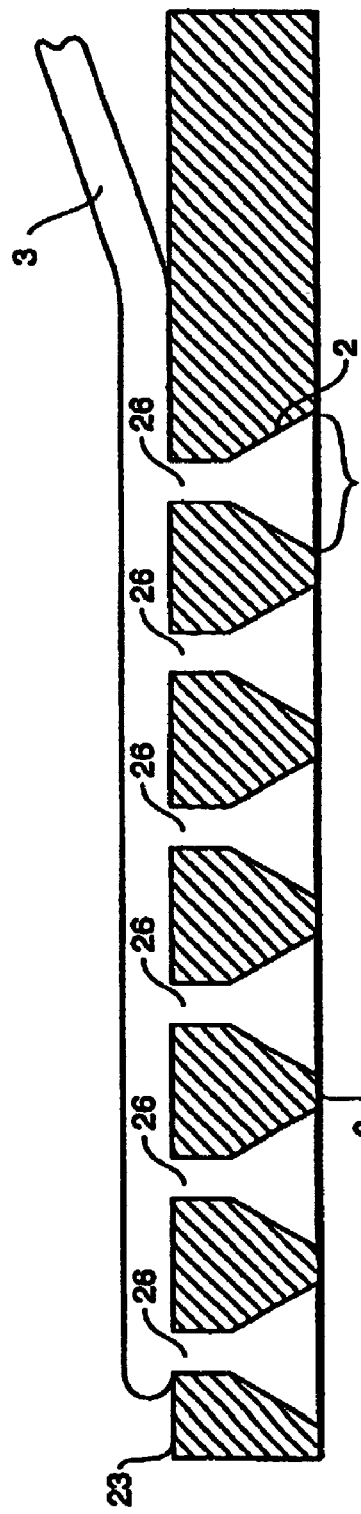
FIGS. 7 and 7A are sectional views of the block showing an alternate configuration for the suction ports and the pressure conducting space.

Referring to FIG. 7, a sectional view of the block 23 through line B-B of FIG. 6 shows the suction ports 2 disposed with the block 23 in a linear array such that each suction port is equidistant from each adjacent suction port 2. The openings 12 of the suction ports 2 are flush with the bottom surface 6 of the block 23. In this embodiment, a pair of vacuum lines 3 connects each suction port 2 to negative pressure via a single passage 26 which runs from the vacuum line 3 to the suction port 2 and is substantially perpendicular to the vacuum line 3. Alternatively, as shown in FIG. 8, a single vacuum line 3 may connect each suction port 2 to negative pressure.

Figure 7A:
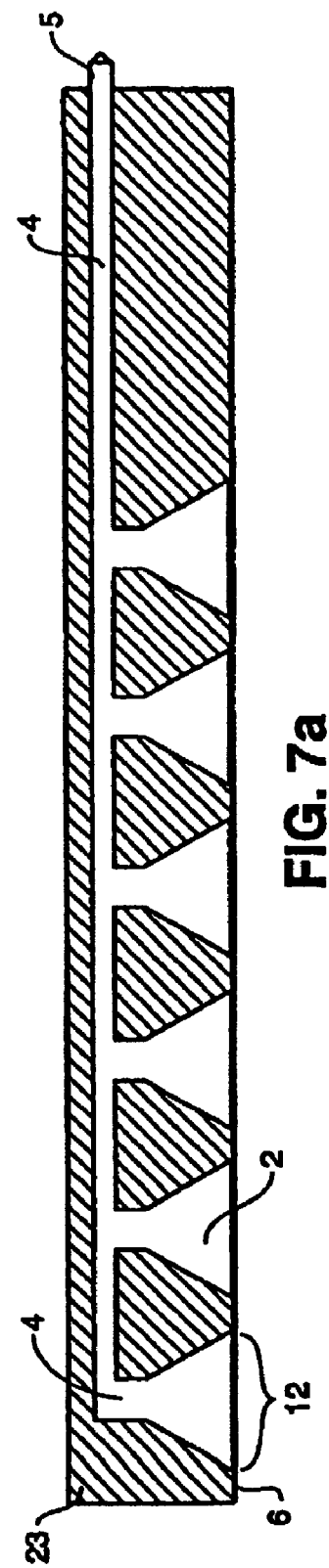
Figure 8:
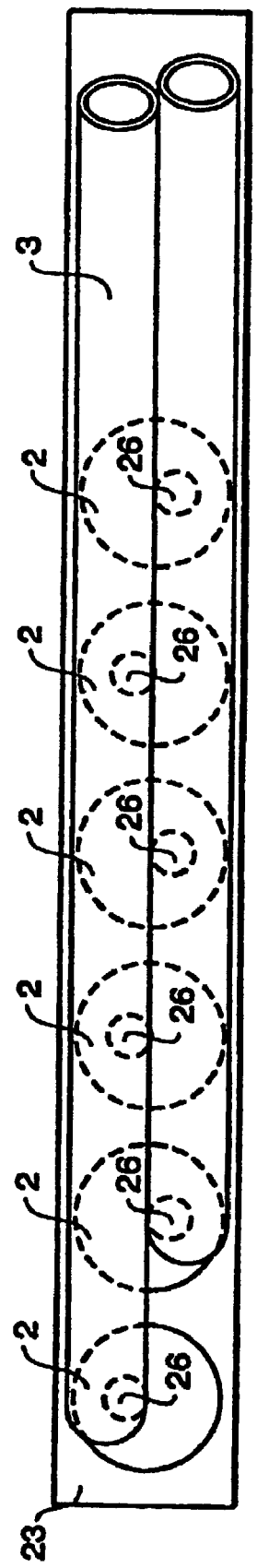
FIG. 8 is an alternative embodiment for an array of suction ports having vacuum tubes which run the length of the block and are oriented to be substantially perpendicular to a passage space leading to each suction port.

Referring to FIG. 7A, the block 23 may also have an inlet 5 which introduces the negative pressure to the suction ports 2. The suction ports 2 are disposed within the bottom surface 6 of the block 23 which is to be affixed to the end of the shaft 21 (see FIG. 5). As will be readily appreciated, the negative pressure can be introduced to the suction ports 2 by a variety of techniques as described above. The vacuum line 3 may be attached to the apparatus 20 at several points such as the individual suction ports as illustrated in FIG. 7 or via a single inlet 5 and communicated to each suction port 2 via pressure conducting space 4 (FIG. 7A) such that the negative pressure is introduced to the block 23 and communicated to each suction port 2. Thus, the objective of communicating the negative pressure to the suction ports 2 to fix the position of the cardiac tissue may be achieved via several alternate techniques which are based on or may be developed from the embodiments disclosed herein.

Figure 9:
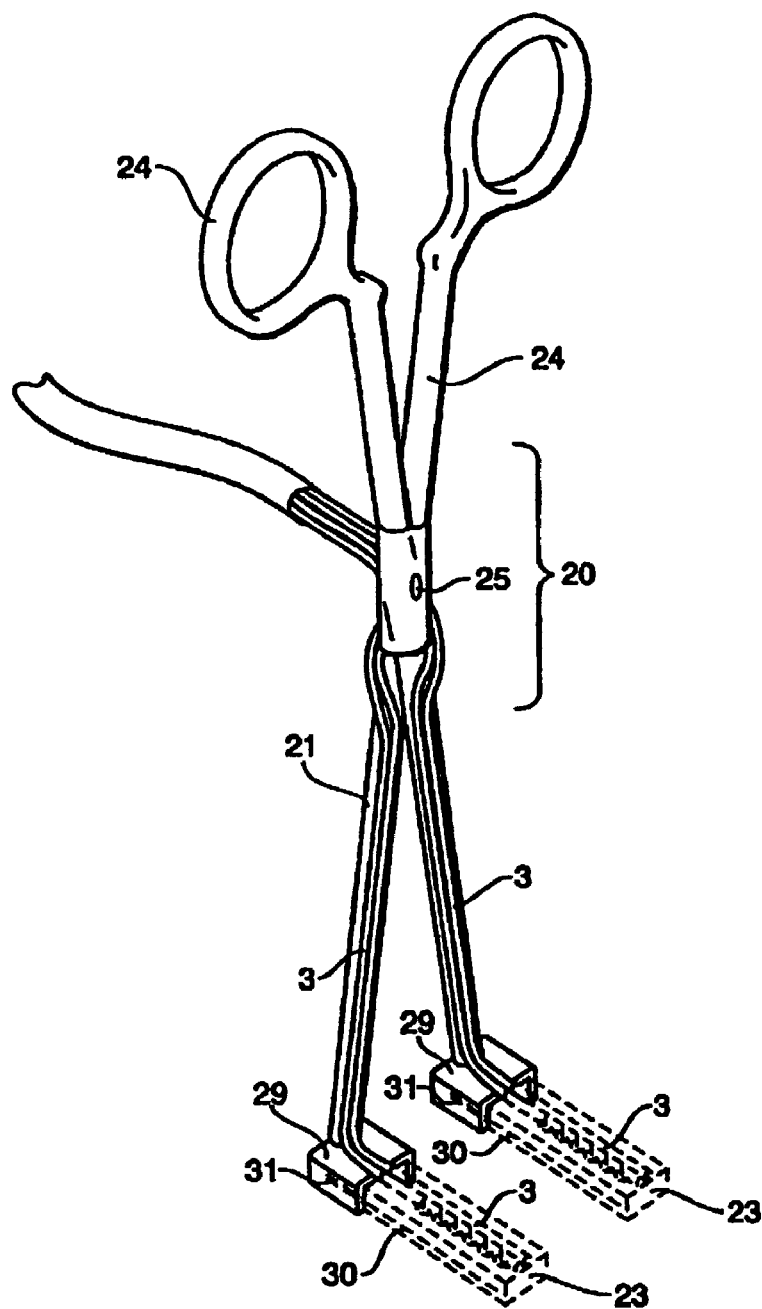
FIGS. 9 and 9A are a hand held instrument having a removable block, wherein the instrument has a receiving means to reversibly receive the block.
Figure 9A:
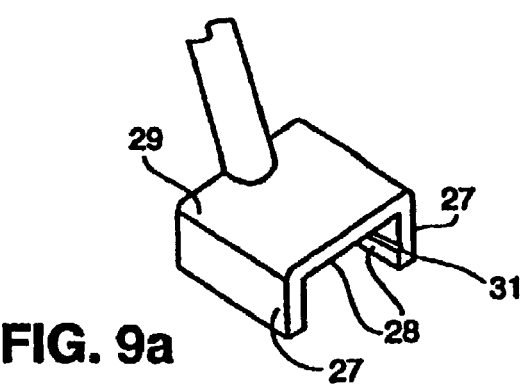

Referring to FIGS. 9 and 9A, as noted above the block 23 may be removable from the apparatus 20. The terminal end of the apparatus 20 has a receiving means 29 which is adapted to reversibly receive the block 23. In a preferred embodiment, the receiving means 29 is comprised of a substantially parallel walls 27 having a grip means 28 associated therewith to maintain the position of the block 23 in place when attached to the receiving means 29. The grip means 28 may be one of several alternate designs. For example, the block 23 may have a ridge or indentation 30 which runs along the lateral exterior surface of the block 23 and fits conformingly in a groove or ridge 31 formed in the interior face of the wall 27.

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims.

The invention claimed is:

1. A method of guiding an instrument relative to an outer surface of a heart, comprising the steps of:
   providing an instrument guide having a plurality of suction ports open to a bottom surface of the instrument guide;
   locating the suction ports in proximity to a target area to be treated;
   applying a negative pressure through the suction ports, thereby applying negative pressure directly to an outer surface of the heart and fixing the instrument guide to the outer surface of the heart;
   introducing at least a portion of the instrument into said instrument guide by traversing a side wall of the instrument guide, such that a location of said at least a portion of the instrument relative to the target area is maintained by said instrument guide; and
   treating the target area with said instrument.

2. The method of claim 1, further comprising introducing at least a portion of a second instrument into said instrument guide such that a location of said at least a portion of the second instrument relative to the target area is maintained by said instrument guide.

3. The method of claim 2, further comprising treating the target area with said second instrument.

4. The method of claim 2, further comprising illuminating the target area with said instrument.

5. The method of claim 2, wherein said first and second instrument portions are introduced at different locations of said instrument guide.

6. The method of claim 5, wherein said first and second instrument portions are introduced through first and second instrument ports in said instrument guide.

7. The method of claim 1, wherein said treating comprises illuminating the target area.

8. The method of claim 1, further comprising fixing said instrument guide to a stable support.

9. The method of claim 8, wherein said fixing comprises fixing said instrument guide to a rib retractor.

10. The method of claim 1, wherein said treating comprises at least one of: cutting, illuminating, suturing, suctioning, blowing and irrigating.

11. The method of claim 1 wherein said instrument comprises a surgical instrument.

12. The method of claim 1, wherein said introducing comprises introducing said at least a portion of said instrument into an attachment means fixed to said instrument guide.

13. The method of claim 1, wherein said introducing comprises introducing said at least a portion of said instrument into a flexible or rigid shaft fixed transversely with respect to a main body of said instrument guide.

14. The method of claim 1, further comprising locking a position of said at least a portion of an instrument relative to said instrument guide.

15. The method of claim 1, wherein the heart is beating.

16. A method of guiding an instrument relative to the outer surface of a heart, comprising the steps of:
   providing an instrument guide having a plurality of suction ports;
   fixing the instrument guide to the outer surface of the heart, in proximity to a target area to be treated, by applying a negative pressure to the outer surface of the heart, through the suction ports in fluid communication with the outer surface of the heart; and
   introducing at least a portion of the instrument into said instrument guide by traversing a side wall of said instrument guide such that a location of said at least a portion of the instrument relative to the instrument guide is maintained by said instrument guide.

17. The method of claim 16, further comprising treating the target area with said instrument.

18. The method of claim 16, further comprising positioning said at least a portion of an instrument relative to the target area.

19. The method of claim 18, wherein said positioning comprises manipulating a shaft attached to said instrument guide, through which said at least a portion of an instrument has been inserted.

20. The method of claim 17, wherein said treating comprises at least one of: cutting, illuminating, suturing, suctioning, blowing and irrigating.

21. The method of claim 16, wherein said instrument comprises a surgical instrument.

22. The method of claim 16, further comprising fixing said instrument guide to a stable support.

23. The method of claim 22, wherein said fixing comprises fixing said instrument guide to a rib retractor.

24. The method of claim 16, further comprising locking a position of said at least a portion of an instrument relative to said instrument guide.

25. A method of guiding an operative element relative to the outer surface of a beating heart, comprising the steps of:
   providing an instrument guide having a plurality of suction ports;
   applying a negative pressure to the suction ports, thereby fixing the instrument guide to the outer surface of the beating heart; and
   introducing at least a portion of the operative element into said instrument guide by traversing a side wall of the instrument guide such that a location of said at least a portion of the operative element relative to the surface of the beating heart is maintained by said instrument guide.

26. The method of claim 25, wherein said operative element comprises a surgical instrument.

27. A method of guiding an instrument relative to the surface of a heart, comprising the steps of:
   providing an instrument guide having a plurality of suction ports;
   locating the suction ports in proximity to a target area to be treated;
   applying a negative pressure to the suction ports, thereby fixing the instrument guide to the surface of the heart;
   introducing at least a portion of the instrument into said instrument guide such that a location of said at least a portion of the instrument relative to the target area is maintained by said instrument guide;
   introducing at least a portion of a second instrument into said instrument guide such that a location of said at least a portion of the second instrument relative to the target area is maintained by said instrument guide; and
   treating the target area with at least one of said first and second instruments.

28. A method of guiding an instrument relative to an outer surface of a heart, comprising the steps of:
   providing an instrument guide having a plurality of suction ports;
   locating the suction ports in proximity to a target area to be treated;
   applying a negative pressure to the suction ports, thereby fixing the instrument guide to the outer surface of the heart;
   introducing at least a portion of the instrument into said instrument guide by traversing a side wall of the instrument guide, such that a location of said at least a portion of the instrument relative to the target area is maintained by said instrument guide; and
   treating the target area with said instrument, wherein said treating comprises illuminating the target area.

29. A method of guiding an instrument relative to the outer surface of a heart, comprising the steps of:
   providing an instrument guide having a plurality of suction ports;
   fixing the instrument guide to the outer surface of the heart, in proximity to a target area to be treated, by applying a negative pressure to the suction ports;
   introducing at least a portion of the instrument into said instrument guide by traversing a side wall of said instrument guide such that a location of said at least a portion of the instrument relative to the instrument guide is maintained by said instrument guide; and
   fixing said instrument guide to a stable support.

* * * * *